(12) United States Patent
Taylor et al.

(10) Patent No.: US 9,986,738 B2
(45) Date of Patent: Jun. 5, 2018

(54) CONTROLLED RELEASE OF SEED AND SOIL TREATMENTS TRIGGERED BY PH CHANGE OF GROWING MEDIA

(75) Inventors: Alan Taylor, Geneva, NY (US); Alexandr Bolotin, Vitebsk (BY); Sarah Pollicove, Rochester, NY (US); Ryan Taylor, Geneva, NY (US)

(73) Assignee: Cornell University, Ithaca, NY (US)

( * ) Notice: Subject to any disclaimer, the term of this patent is extended or adjusted under 35 U.S.C. 154(b) by 980 days.

(21) Appl. No.: 13/642,343

(22) PCT Filed: Apr. 21, 2011

(86) PCT No.: PCT/US2011/033420
§ 371 (c)(1),
(2), (4) Date: Nov. 27, 2012

(87) PCT Pub. No.: WO2011/133765
PCT Pub. Date: Oct. 27, 2011

(65) Prior Publication Data
US 2013/0065755 A1    Mar. 14, 2013

Related U.S. Application Data

(60) Provisional application No. 61/326,363, filed on Apr. 21, 2010.

(51) Int. Cl.
*A01N 43/68* (2006.01)
*C07D 417/06* (2006.01)
(Continued)

(52) U.S. Cl.
CPC ............. *A01N 43/68* (2013.01); *A01N 25/00* (2013.01); *A01N 25/10* (2013.01); *C07D 417/06* (2013.01)

(58) Field of Classification Search
CPC ........ A01N 43/68; A01N 25/00; A01N 25/10; C07D 417/06
(Continued)

(56) References Cited

U.S. PATENT DOCUMENTS

| 6,015,571 A | 1/2000 | Scher et al. |
| 6,077,522 A | 6/2000 | Scher et al. |
| 6,776,996 B2 | 8/2004 | Sun et al. |

FOREIGN PATENT DOCUMENTS

| CN | 1135160 A | 11/1996 |
| CN | 1218617 A | 6/1999 |

(Continued)

OTHER PUBLICATIONS

Avicel CL611: retrieved from internet: www.signetchem.com/downloads/.../Avicel-Cl-611-Specifications.pdf. Retrieved on Jun. 2, 2014.*

(Continued)

*Primary Examiner* — Hong Yu
(74) *Attorney, Agent, or Firm* — Clark & Elbing LLP (57) ABSTRACT

The invention features a method of improving the growth of a plant, involving applying to a seed or locus thereof a composition comprising an active ingredient and a pH-dependent film-forming polymer, followed by exposing the composition to an appropriate pH to release said active ingredient. The invention further features a seed including a composition having a) an active ingredient; and b) a pH-dependent film-forming polymer. Additionally, the invention features a seed treatment composition that includes a) an agrochemical; b) a pH-dependent film-forming polymer; and c) a seed coating agent.

19 Claims, 3 Drawing Sheets

(51) Int. Cl.
*A01N 25/00* (2006.01)
*A01N 25/10* (2006.01)

(58) Field of Classification Search
USPC .............................. 504/100, 234; 514/229.2
See application file for complete search history.

(56) References Cited

FOREIGN PATENT DOCUMENTS

| EP | 0187341 A1 | 7/1986 | | |
|---|---|---|---|---|
| EP | 0890308 B1 | 1/1999 | | |
| WO | WO 2007/072052 A2 * | 6/2007 | ............. | A01N 51/00 |
| WO | WO-2008/155097 A2 | 12/2008 | | |

OTHER PUBLICATIONS

Written Opinion of the International Searching Authority for International Patent Application No. PCT/US11/33420, dated Jul. 15, 2011 (7 pages).
International Preliminary Report on Patentability for International Patent Application No. PCT/US11/33420, dated Oct. 23, 2012 (8 pages).
International Search Report for International Patent Application No. PCT/US11/33420, dated Jul. 15, 2011 (3 pages).
First Office Action for Chinese Patent Application No. 201180030862.3, dated Aug. 21, 2013 (37 pages) (English Language Translation Included).
Second Office Action for Chinese Patent Application No. 201180030862.3, dated Jun. 26, 2014 (23 pages) (English Language Translation Included).

* cited by examiner

CONTROLLED RELEASE OF SEED AND SOIL TREATMENTS TRIGGERED BY PH CHANGE OF GROWING MEDIA

CROSS-REFERENCE TO RELATED APPLICATIONS

This application is the U.S. National Stage filing under 35 U.S.C. § 371 of International Application No. PCT/US2011/033420, filed Apr. 21, 2011, which claims the benefit of U.S. Provisional Patent Application No. 61/326,363, filed Apr. 21, 2010.

BACKGROUND OF THE INVENTION

The present invention relates to the controlled release of seed and soil treatments.

Efficient use of agricultural chemicals has become increasingly important in efforts to improve plant nutrition and pest management, and to decrease environmental contamination. Fertilizers and pesticides are important chemicals for providing newly planted crops a healthy start. Fertilizers promote growth, reduce stress, and provide necessary nutrition. Pesticides protect against damaging pests such as insects or pathogens. Timing of the application of such chemicals affects plant growth and development. Consequently, there is a need in agriculture for compositions and methods that provide for controlled release of such agricultural chemicals. The present invention fulfills such agricultural needs.

SUMMARY OF THE INVENTION

In one aspect, the invention features a method of improving the growth of a plant, the method, in general, includes applying to a seed or locus thereof a composition including an active ingredient and a pH-dependent film-forming polymer, followed by exposing the composition to an appropriate pH to release the active ingredient. In various embodiments, the composition is a microcapsule; the active ingredient is an agrochemical, an attractant, a repellent, or a bait; the agrochemical is a pesticide, insecticide, nematicide, acaricide, miticide, bactericide, fungicide, herbicide, a plant growth regulator, or a fertilizer; the pesticide is abamectin or thiamethoxam; the fungicide is mefenoxam, fludioxonil, a strobilurin, thiabendazole, or a triazole; the herbicide is atrazine; and the plant growth regulator is a triazole selected from the group consisting of uniconazole, paclobutazol, cyproconazole, propiconazole, and trinexapac-ethyl.

In other embodiments, the pH-dependent film-forming polymer is a polyacrylamide, a cellulose ester phthalate (for example, cellulose acetate phthalate), cellulose ether phthalate (for example, methylcellulose phthalate, hydroxypropyl cellulose phthalate, hydroxypropyl methylcellulose phthalate), polyvinyl acetate phthalate, cellulose acetate trimellitate, hydroxypropyl methylcellulose acetate succinate, shellac, ammoniated shellac; a cross-linked amino resin based on urea-formaldehyde, melamine-formaldehyde, benzoguan-formaldehyde, glycoluril-formaldehyde, or etherified ones with incorporated free carboxylic groups or base-cleavable ester or thioester moiety; acrylic and methacrylic acids and their esters copolymers such as methyl acrylate-methacrylic acid copolymer, methyl methacrylate-methacrylic acid copolymer (Eudragit® S100), or methacrylic acid-methyl acrylate-methyl methacrylate copolymer (Eudragit® FS 30D).

In still other embodiments, the plant is a vegetable plant (for example, tomato, pepper, spinach, lettuce, asparagus, cabbage, broccoli, cauliflower, carrots, onions, potatoes, cucumbers, melons, squash and pumpkin), an ornamental plant (for example, flowers, turf, shrubs, broad-leaved trees and evergreens, such as conifers), a cereal (for example, wheat, barley, rye, oats, corn, rice, sorghum, triticale and related crops); a beet (for example, sugar beet and table beet); a leguminous plant (for example, beans, lentils, peas, soybeans); or an oil plant (for example, canola, rape, mustard, sunflowers).

In each of the aforementioned embodiments, the invention provides methods for improving growth which includes improving the vigor of the plant; combating or controlling pests of the plant; or both.

According to the aforementioned methods, the composition is applied to the seed and the locus is soil (for example, a field soil or a media for growing plants). Compositions useful in these methods include at least one and preferably two or more active ingredients. In one embodiment, the composition further includes an inert carrier such as microcrystalline cellulose and porous or non-porous particulates. In another embodiment, the agrochemical is dispersed in or applied to the inert carrier. In still another embodiment, the agrochemical is encapsulated by the pH-dependent film-forming polymer.

In another aspect, the invention features a seed that includes a composition including: a) an active ingredient; and b) a pH-dependent film-forming polymer. In general, the composition is applied to the seed according to standard methods known in the art. In one embodiment, the composition includes microcapsules.

In another aspect, the invention features a method of combating and controlling pests affecting a seed or plant which includes applying to the pests or to the locus of the pests, or to the seed or plant susceptible to attack by a pest, or to the plant propagation material an effective amount of a composition including an active ingredient and a pH-dependent film-forming polymer, followed by exposing the composition to an appropriate pH to release the active ingredient.

In another aspect, the invention features a method of initially protecting a seed or plant from exposure to a phytotoxic compound or a compound that may have phytotoxic properties by providing an effective amount of a composition including an active ingredient and a pH-dependent film-forming polymer, followed by exposing the composition to an appropriate pH to release the active ingredient.

A method of fertilizing a plant or plant propagation material or locus thereof which includes applying to the locus an effective amount of a composition including an active ingredient and a pH-dependent film-forming polymer, followed by exposing the composition to an appropriate pH to release the active ingredient from the composition.

In yet another aspect, the invention features a method for the controlled release of an active ingredient in a soil including the steps of: a) providing a composition including i) an active ingredient; and ii) a pH-dependent film-forming polymer; wherein the composition controllably releases the active ingredient in the presence of a solution having an appropriate pH; b) placing the composition including the active ingredient in the soil; and c) exposing the composition to the solution having an appropriate pH, whereupon the active ingredient is controllably released from the composition ingredient in the soil.

In still another aspect, the invention features a seed treatment composition including: a) an agrochemical; b) a pH-dependent film-forming polymer and c) a seed coating agent.

In another aspect, the invention features a method of treating seed, the method includes applying an effective amount of a composition that includes: a) an agrochemical; b) a pH-dependent film-forming polymer and c) a seed coating agent to a batch of seeds. In one embodiment, the seeds are substantially dry before the effective amount of the composition is applied. In another embodiment, the seeds are seeds of a vegetable plant (for example, tomato, pepper, spinach, lettuce, asparagus, cabbage, broccoli, cauliflower, carrots, onions, potatoes, cucumbers, melons, squash and pumpkin), an ornamental plant (for example, flowers, turf, shrubs, broad-leaved trees and evergreens, such as conifers), a cereal (for example, wheat, barley, rye, oats, corn, rice, sorghum, triticale and related crops); a beet (for example, sugar beet and table beet); a leguminous plant (for example, beans, lentils, peas, soybeans); or seeds of an oil plant (for example, canola, rape, mustard, sunflowers). In still another embodiment, the method further includes the step of exposing the composition to a solution having an appropriate pH, whereupon the agrochemical is controllably released from the composition.

In another aspect, the invention features a seed coated with an agrochemical; a pH-dependent film-forming polymer and a seed coating agent.

The invention further features the use of a composition that includes an agrochemical; a pH-dependent film-forming polymer and a seed coating agent.

The invention also features use of a composition including an active ingredient and a pH-dependent film-forming polymer in a soil.

By "microcapsule" is meant a particle of agrochemical or composition of agrochemical with inert particulate carrier that is encapsulated with a pH-dependent film-forming polymer.

By "plant propagation material" is meant all the generative parts of the plant, such as seeds, which can be used for the multiplication of the plant and vegetative plant materials such as cuttings and tubers (for example, potatoes). Accordingly, as used herein, part of a plant includes plant propagation material itself. The phrase also includes roots, fruits, tubers, bulbs, and rhizomes. Germinated seedlings and young plants, which are to be transplanted after germination or after emergence from the soil (for example, transplant crops), are also included in the phrase "plant propagation material."

By "locus" is meant a place where a plant grows, where plant propagation material are sown, or where plant propagation material will be placed into the soil. An example of a locus is a field on which a crop plant is growing.

By "weed" is meant any undesired plant, and thus includes not only agronomically important weeds but also volunteer crop plants.

By "improving the vigor" of a plant relates to an increase or improvement of the vigor rating, or the stand (the number of plants per unit of area), or the plant height, or the plant canopy, or the visual appearance (such as greener leaf color), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method or composition.

The invention also provides a method of improving the growing characteristics of a plant, which includes applying to a seed, or applying to soil, or applying to a plant, seed, seedling, or plant propagation material, a composition described herein, in any desired sequence or simultaneously.

The invention provides a number of important advances and advantages. For example, controlled release of an active ingredient (AI) is readily triggered at any desirable moment of time simply and reproducibly by adjusting the soil medium pH, a parameter that is easily controlled, for example, in a greenhouse growing medium. The use of a triggered controlled release formulation further allows for a lag phase (a period when AI is not released) that is typically greater than a greenhouse growth period, for example, of approximately 3-6 weeks. This feature is especially useful for preventing loss of AI administered to transplant crops (for example, tomato) before such crops are transferred to the field. Further, a solution used to trigger AI release is readily designed to provide additional benefits to plants. For example, one solution that can be used to trigger AI release is a phosphate buffer solution (PBS), which also provides necessary phosphorous and potassium for plant growth and nourishment. The compositions disclosed herein are also easily fashioned for application to seeds using conventional seed-coating technology. The compositions may also be provided in plugs or pots. Accordingly, the present invention has broad application for controlled-release formulations of AI in an array of agricultural settings.

Other features and advantages of the invention will be apparent from the following description, and from the claims.

DETAILED DESCRIPTION

Overview

In general, the invention features controlled release delivery systems designed for the triggered release of an active ingredient (AI) in agricultural applications. This is accomplished using a composition having an AI in combination with a pH-dependent film-forming polymer. A pH-dependent film-forming polymer is typically coated on the AI solid core to provide desirable pH-dependent release characteristics as is described herein. Generally, a core of a solid material (for example, a carrier coated with an AI or infused with an AI, or a solid AI) is coated with a pH-dependent water soluble polymer. The AI is subsequently released from the composition by a pH-dependent trigger (i.e., a base to acid or preferably an acid to base transition in a certain pH range; in particular, the compositions are acidic (≤6.5 pH)), allowing fine temporal control of AI administration to a seed, seedling, plant, or plant propagation material, or a locus thereof. One advantage of such a system is that the timing of AI release is readily controlled by changing the pH of media (for example, soil) using standard reagents. Exemplary solutions capable of releasing an AI include potassium phosphate buffer or PBS (phosphate buffer solution) with a pH≥7 or a dilute alkaline solution such as KOH.

In addition, the delivery systems described herein may be formulated in virtually any convenient size range that can be applied as a seed treatment or directly dispersed in soil.

Carriers

Carriers such as inert carriers useful in the invention include, for example, microcrystalline cellulose (MCC) and porous or non-porous particulates. Such carriers, typically 10 µm-3 mm, may be coated or infused, as needed, with an AI according to standard methods known in the art, for example, as described in the Examples (below). Other inert materials include finely divided mineral substances such as pumice, attapulgite, bentonite, kaoline zeolite, diatomite, and other clays, modified diatomaceous adsorbents, charcoal, vermiculite, finely divided organic substances such as peat moss, wood powder, and porous ceramic particles.

Such materials are commercially available and known in the art.

Active Ingredients and Formulations

One skilled in the art will recognize that the present systems are applicable to the triggered delivery of a wide range of AIs. Such AIs include, for example, agrochemicals (for example, pesticides, nematicides, acaricides, miticides, bactericides, fungicides, herbicides, plant growth regulators or fertilizers), attractants, repellents, and baits. The AI can be of any type, or a mixture of different types, preferably at least one AI in a formulation exhibits pesticide efficacy. Solid AIs may, if desired, be used without an inert carrier. Combinations of AIs in a formulated composition are also useful in the invention. AIs exclude a biological such as Pseudomonas. Typical AIs and other components are, without limitation, as follows.

Exemplary pesticides useful in a pH-triggered control release composition include abamectin or thiamethoxam.

Exemplary fungicides include mefenoxam, fludioxonil, a strobilurin, thiabendazole, or a triazole.

Herbicides that are phytotoxic and other compounds with phytotoxic properties.

Naturally-occurring plant growth regulators include abscisic acid, auxins, cytokinins, ethylene, gibberellins, and salicylic acid. Plant growth regulators also include man-made compounds, such as triazoles. Exemplary triazoles include uniconazole, paclobutazol, cyproconazole, propiconazole, and trinexapac-ethyl.

Attractants and repellents include respectively pheromones and essential oils such as thyme or garlic.

Baits include sucrose plus spinetoram/spinosad.

Formulations of an AI or combinations of AIs may also include auxiliary components known in the art of agrochemical formulations in customary amounts.

For example, the compositions may also include alkali metal, alkaline earth metal, metal, or ammonium salts. Zinc chloride and alkali metal, alkaline earth metal, or ammonium salts of mineral acids, especially nitrates, phosphates, sulfates, chlorides, and carbonates of sodium, potassium, ammonium, magnesium, and calcium are preferred.

Such compositions may additionally include micronutrients to aid in the nourishment and health of the plant and/or plant propagation material. Suitable micronutrients include, but are not limited to, chlorine (Cl), zinc (ZN), boron (B), copper (Cu), iron (Fe), manganese (Mn) or molybdenum (Mo). Micronutrients may be supplied in chelate form according to methods known in the art.

Depending upon the particular plant or plant propagation material to be treated, the conditions under which it is to be stored, and the soil and weather conditions under which it is expected to germinate and grow, the compositions of the present invention may include a wide spectrum of one or more additives. Such additives include, but are not limited to, uv-protectants, pigments, dyes, extenders such as flour, dispersing agents, excipients, anti-freezing agents, preservatives, herbicidal safeners, seed safeners, seed conditioners, surfactants, sequestering agents, plasticizers, colorants, brighteners, emulsifiers, flow agents such as calcium stearate, talc and vermiculite, coalescing agents, defoaming agents, humectants, thickeners, waxes, and fillers. Such additives are commercially available and known in the art.

pH-Dependent Film-forming Polymers

AIs or an AI inert carrier mixture is coated with a pH-dependent film-forming polymer according to methods known in the art. For example, fluidized bed coating techniques or other standard methodologies such as encapsulation technologies, for example, spray drying, hot melt extrusion, and microemulsification, used in the pharmaceutical industry, are useful for the coating of small particles to make controlled-release formulations. Machinery useful for applying such coatings typically are fluid-bed machines having Wurster-type equipment (where particles circulate while being sprayed) that allow for the coating of particles as small as 50 µm in diameter and result in a uniform polymer film with a smooth surface.

In one embodiment, the compositions of the present invention are in the form of coated particles or coated multiparticulates. Accordingly, the compositions are film coated using a coating composition comprising at least one film forming agent which includes a pH dependent water soluble polymer.

In general, a core of a solid material of a size of from 10 µm-3 mm is coated with a pH-dependent water soluble polymer by a spray process. A solution containing the pH-dependent water soluble polymer is then sprayed onto the solid material and the solvent is evaporated. The amount of the pH-dependent film-forming polymer is in the range of from 0.15 to 0.40 g per 1 g of particles.

Polymer coating of particles is accomplished using any standard method. For example, particles formed of a solid AI or an AI inert carrier mixture is coated with a pH dependent water soluble polymer mixture as described in the Examples (below). The polymer mixture is dissolved in a solvent such as water, a ketone such as acetone or methyl ethylketone or an alcohol such as ethanol and/or mixtures thereof. The solution is then subsequently sprayed onto the particles using standard fluidized bed equipment. The solution is sprayed onto the particles for a sufficient period of time, such as from 2 to 480 minutes. The time required is dependent on the batch size and the desired thickness of the polymer film. The batch size may be from 5 g up to 500 kg.

Exemplary pH-dependent film-forming polymers include a variety of polymeric compounds whose solubility in an aqueous solution varies with the pH of the solution. A pH-dependent film-forming polymer can either be acid-labile (soluble below a threshold pH) or base-labile (soluble above a threshold pH).

Such pH-dependent film-forming polymers are polyacrylamides, phthalate (such as phthalic acid (an aromatic dicarboxylic acid) and mono- and di-esters thereof) and cellulose derivatives (for example, polyvinyl acetate phthalate, cellulose acetate phthalate, methylcellulose phthalate, hydroxypropyl cellulose phthalate, hydroxypropyl methylcellulose phthalate, cellulose acetate trimellitate, and hydroxypropyl methylcellulose acetate succinate), shellac and its derivatives (for example, ammoniated shellac), cross-linked resins based on formaldehyde (for example, those based on urea-formaldehyde, melamine-formaldehyde, benzoguan-formaldehyde, glycoluril-formaldehyde, or ether and thioester derivatives thereof), and acrylic polymers (for example, methacrylic acid and ester copolymers and their derivatives).

Acrylate polymers are a class of polymers formed from monomers of acrylic acid and its derivatives (for example, methacrylic acid, methyl-acrylate, and methyl-methacrylate) are especially useful. Because acrylic acid has a highly reactive double-bond, it easily reacts to form polymers and co-polymers. Particularly useful pH-dependent film-forming polymers are copolymers such as methyl acrylate-methacrylic acid copolymer, methyl methacrylate-methacrylic acid copolymer (trade name Eudragit® S100), and methacrylic acid-methyl acrylate-methyl methacrylate copolymer (trade name Eudragit® FS 30D).

Eudragit® copolymers are available commercially from Evonik Industries (Darmshadt, Germany). Eudragit® FS 30D is an anionic copolymer that exists as an aqueous dispersion. It is insoluble in acidic media, but dissolves at higher pH (above a pH of 7.0) due to salt formation. Eudragit® FS 30D is a flexible polymer, with a glass transition temperature of 48° C. The average molecular weight of Eudragit® FS 30D is approximately 220 kilodaltons.

To coat a substance of interest, Eudragit®FS 30D is prepared as a spray suspension using Plasacryl® T20 or any anti-tacking agent, plasticizer or glidant that eases the flowability of the Eudragit® dispersion. A general composition contains 60% Eudragit®, 10% Plasacryl® T20, and 30% water. The resulting spray suspension can be applied to any particle of interest containing the AI using a fluid bed coater or any desired method of coating. After the appropriate application period microcapsules are, if desired, cured by heating. Additional details of microcapsule formation are described in the examples that follow.

The compositions provided herein may be a fabricated multiparticulate-controlled release device, which include, in general, a multiplicity of particles or other such devices including granules, or pellets, microparticulates, beads, microcapsules and microtablets, or core pellets ranging from about 10 μm to about 3 mm, about 50 μm to about 2.5 mm, or from about 100 μm to 1 mm or even 3 mm or more in diameter.

Application

The rates of application or use of an AI-containing composition varies, for example, according to type of use, type of crop, the density of the planting, the specific active ingredients in the composition, type of plant propagation material or plant but is such that the AI is in an effective amount to provide the desired action (such as disease or pest control, fertilizing action, or plant growth regulating capabilities or application of an AI with phytotoxic properties) and can be determined, if necessary, by trials well known in the art.

With respect to seed treatment, AI-containing compositions can also include or may be applied together and/or sequentially with further active compounds. Such further useful active compounds can be fertilizers or micronutrient donors (such as Mo, Zn and/or Co) or other preparations that influence plant growth, or plant inducers.

In another working example, pH-triggered compositions can be used as pesticide-containing seed coatings for transplant crops. Transplant crops are typically initially grown in the greenhouse and later transferred to the field, where they fare better than bareroot transplants. The greenhouse growth period can last approximately 3-6 weeks. During this period, AIs applied to seeds may leach away in greenhouse media, and be gone when the transplants are moved to the field. This problem can be circumvented by using a pH-dependent film-forming polymer to encapsulate the AI. Because soil conditions in the greenhouse are typically acidic, the AI is not released. After transplants are transferred to the field, AI release can be triggered using the basic solution PBS (potassium phosphate buffer).

Methods for applying AI-containing compositions to plant propagation material, especially seeds, are known in the art. These methods include seed coating, encrusting, and pelleting application methods of the propagation material. The AI-containing compositions can be applied to the seed at any time after harvest of the seed and before it is sown in a greenhouse or a field. Such methods are well known in the art.

A seed coating composition is maintained at an acidic pH (≤6.5). Similarly, the pH of a microcapsule and soil media are maintained at an acidic pH (≤6.5).

Seeds of agriculturally important plants useful in the invention include, for example, a vegetable plant (for example, tomato, pepper, spinach, lettuce, asparagus, cabbage, broccoli, cauliflower, carrots, onions, potatoes, cucumbers, melons, squash and pumpkin), an ornamental plant (for example, flowers, turf, shrubs, broad-leaved trees and evergreens, such as conifers), a cereal (for example, wheat, barley, rye, oats, corn, rice, sorghum, triticale and related crops), a beet plant (for example, sugar beet and table beet), a leguminous plant (for example, beans, lentils, peas, soybeans), or an oil plant (for example, canola, rape, mustard, sunflowers).

Application of an AI-containing composition to a fruit is also contemplated. Exemplary fruits include, without limitation, apples, pears, oranges, grapes, plums, tomatoes, melons (for example, watermelon, honeydew, and cantaloupe), berries (strawberry, blackberry, raspberry, blueberry, currant, elderberry, honeysuckle), pineapples, pomegranates, and bananas.

Agricultural applications of the present compositions and methods include their use to protect any of the above plants against pests.

One skilled in the art will recognize many similar agriculturally important applications exist for the methods and compositions of the present invention. For example, pH-triggered release is also applicable to loci of seeds, for example, in a soil, plugs, pots, or in a field.

Release

Accurate timing of AI application is an important key to providing a plant with nutrients or to control pests. According to the methods described herein, triggered release of an AI from a composition described herein is affected by dissolving a film-forming polymer based on application of a solution having a specified pH. For example, AIs coated in Eudragit® FS 30D may be released by applying a phosphate buffered solution (PBS) (>pH 7). The release composition, in general, may be a buffered solution (i.e., a solution having a defined pH regulated by a pre-determined ratio of a weak acid or base and its conjugate). Alternatively, a dilute alkaline solution such as KOH may be used as a release trigger.

Depending on the application, the release composition may be applied to the seed, or locus thereof to release the active ingredient from at least 30 seconds to about 6 weeks after the composition containing the active ingredient and pH-dependent film-forming polymer are applied.

The release composition is administered with watering once or in batches at various intervals depending on the application. Alternately, a release agent may be administered as a solid, liquid, aqueous solution, emulsion, or other homogeneous or heterogeneous mixture.

The effects of the release composition on the pH of the desired media may be monitored using conventional means (for example, pH meters and pH strips or release of AI), and the addition of release composition stopped when a desired pH is reached. The release composition may be pre-mixed with water and delivered to the plants during watering. Preferably, the release composition also provides other benefits (for example, nutritional benefits) to the plant. PBS provides plants with phosphorus and potassium. Such release compositions may additionally include micronutrients to aid in the nourishment and health of the plant and/or plant propagation material. Suitable micronutrients include, but are not limited to, zinc (Zn), boron (B), copper (Cu), iron (Fe), manganese (Mn) or molybdenum (Mo). Micronutrients may be supplied in chelate form according to methods known in the art.

A release composition is applied using drip irrigation with an injector according to methods known in the art. Drip irrigation, in particular, provides for precise timing and application of the release composition.

Having described the invention, there now follow particular examples of the invention. These examples are provided for the purpose of illustrating the invention, and should not be construed as limiting.

EXAMPLES

Example 1

Triggered Release of Rhodamine B

Rhodamine B was used as a model AI due to its water solubility, intense color, and fluorescence at low concentrations that makes the release of the AI visual at early stages.

Rhodamine-loaded MCC were prepared by spraying a dye solution (0.3 g of Rhodamine, 80 mL of ethanol, 20 mL of water) onto 1 mm MCC (100 g) in a conventional coating pan. The dye-loaded MCC were coated with Eudragit® FS 30D to produce microcapsules according to standard methods used in pharmaceutical formulation preparation.

In a vessel, the amount of water of approximately 25 g was heated to 65° C. on a hot plate. Glycerylmonostearate (GMS), serving as a glidant, was added by slow mixing using a magnetic stirrer. The temperature was maintained around 60° C. until the GMS melted. The vessel was subsequently removed from the hot plate and GMS was homogenized with a high shear ultra-turrax mixer for about 40 minutes. Next, 0.4 g of emulsifier Tween® 80 was added and the mixture was homogenized for 20 minutes followed by the addition of 0.5 g of triethyl citrate, which served a plasticizer. The GMS suspension obtained was added to the Eudragit® FS 30D dispersion (about 41 g) and the mixture was gently stirred for up to 20 minutes to formulate a spray dispersion. The solid content of the spray dispersion was about 20% w/w. This dispersion was applied for coating 60 g of rhodamine-loaded MCC in a coating pan. During the coating process, the temperature was maintained at about 35° C. The coated microcapsules were then tumbled for 3 hours. The microcapsules were then placed into an oven and left at 40° C. for 24 h for curing.

A rhodamine release study in a solution was carried out in static media as follows. The amount of 0.25 g of Eudragit®-coated MCC microcapsules was placed into a glass container and 100 mL of a phosphate buffer solution (PBS) with different pH values (6.0, 6.5, 6.8, 7.0, 7.5) were added. At predetermined time points, the concentration of rhodamine in dissolution media was determined using a Beckman DU-64 UV-VIS spectrophotometer, with the absorbance being measured at the wavelength of 556 nm. Just before determination, each medium was gently stirred with a glass rod and allowed to settle down.

The rhodamine release study in soil was conducted as follows. Several containers were filled in with different kinds of soil. The amount of 0.6 g of Eudragit®-coated MCC microcapsules were uniformly distributed on the surface and covered with a small amount of soil. The samples were watered using deionized water for up to 10 days. Then PBS (pH 7.8) was applied for watering experimental samples for 1 day at a particular time, while deionized water continued to be used for controls. Both controls and experiments were then watered with deionized water for 2 more days to move the dye further into the soil layer. Containers were then cut in half lengthwise and samples were dried. The release and movement of rhodamine in the soil layer were estimated visually according to the dye's fluorescence under a conventional longwave UV lamp. In some cases ethanol or a 1% Laponite solution was used to enhance the fluorescence by spraying them on the soil surface.

Figure 1:
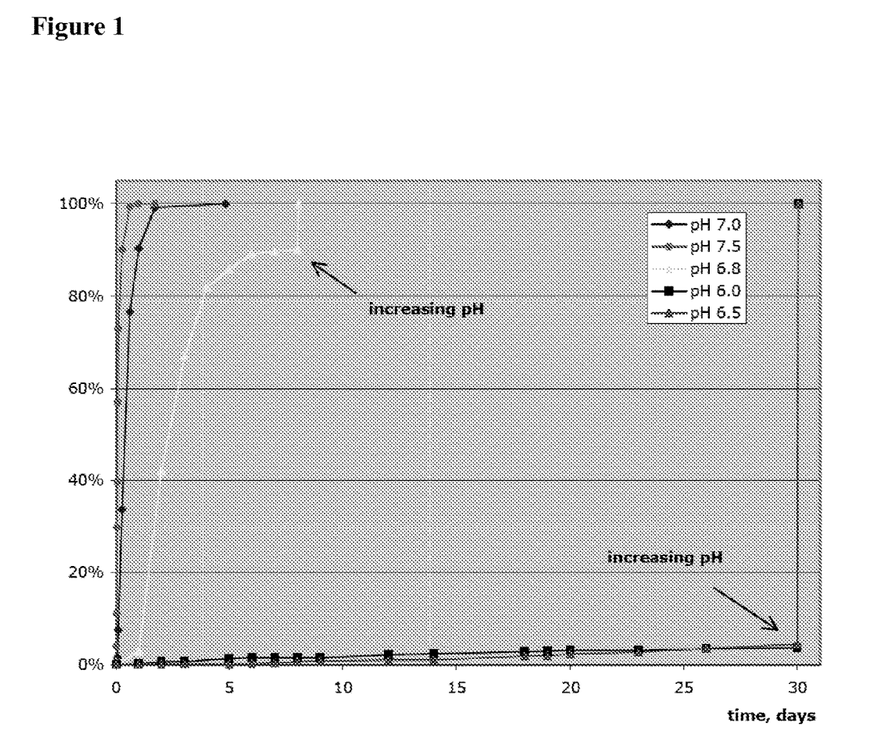
FIG. 1 is a graph of release rates of rhodamine B from microcapsules produced from MCC coated with Eudragit® FS 30D in media of various pH.

FIG. 1 shows the release of rhodamine B from microcapsules produced from MCC coated with Eudragit® FS 30D after applying PBS (pH 7.8).

Figure 2:
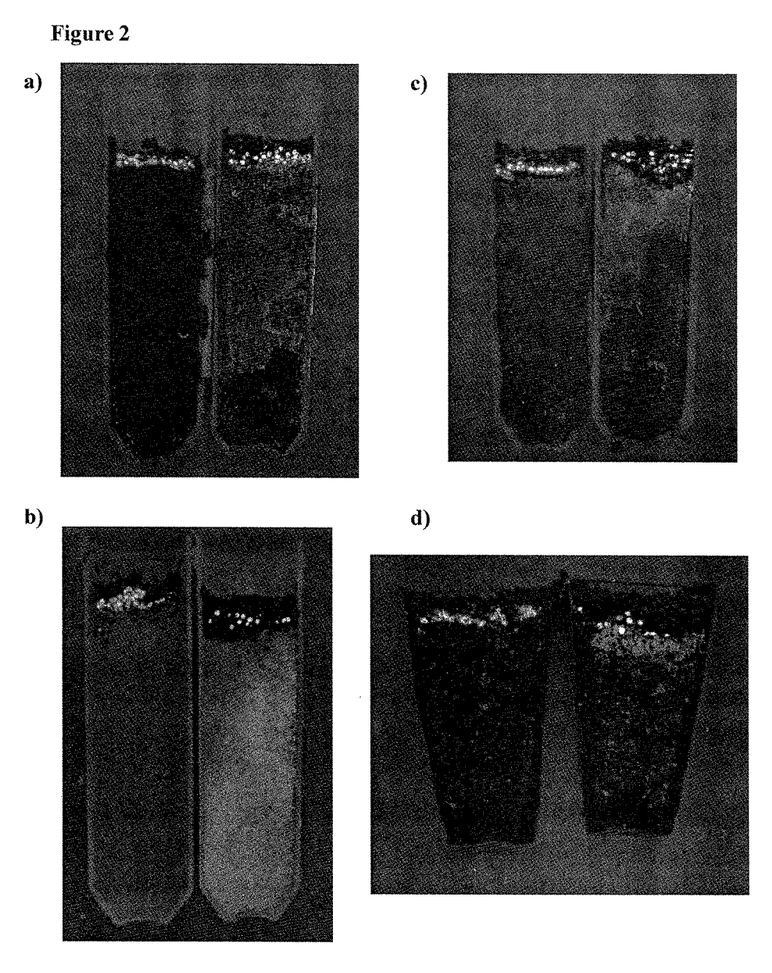
FIG. 2 shows the release of rhodamine B from microcapsules produced from MCC coated with Eudragit® FS 30D after applying PBS (pH 7.8) solution in different soil media: a) sandy loam soil from Phelps, N.Y.; b) white sand; c) builder's sand; and d) Redi-earth.

FIG. 2 shows the release of Rhodamine B from microcapsules produced from MCC coated with Eudragit® FS 30D after applying PBS (pH 7.8) in different kinds of soil media: sandy loam; white sand; builder's sand; and Redi-earth.

Example 2

Microencapsulation of the Active Ingredients

To conduct microencapsulation of different active ingredients for triggered release using fluidized bed technology.

Microcrystalline cellulose (MCC) particles were used as the inert carrier for the application of several agricultural pesticides: thiamethoxam, an insecticide and abamectin, an insecticide and nematicide. Three controlled release microcapsule samples were prepared: two formulations of thiamethoxam, Cruiser 5 FS and Cruiser 70 WS, and one formulation of abamectin, Avicta 400. Each active ingredient was mixed with water and sprayed onto the MCC using fluidized bed equipment. Each treatment was then coated with Eudragit® FS 30D dispersion with glycerol monosterate, tween 80, triethyl citrate and water to form microcapsules. Thiamethoxam or abamectin active ingredient concentration was 5% (wt/wt) of the microcapsule.

Example 3

Triggered Release of Atrazine in Tomato Plants

To conduct a study on the triggered release of AI under greenhouse conditions, 1 mm MCC particles were loaded with the herbicide atrazine as follows.

Atrazine-loaded MCC particles were prepared by spraying a solution (0.2 g of atrazine, 80 mL of ethanol, 20 mL of water) onto 1 mm MCC (100 g) in a conventional coating pan. The atrazine-loaded MCC were coated with Eudragit® FS 30D the same way as described for Rhodamine in Example 1.

Tomato 'Facundo' seeds were sown in Speedling® 32-plant trays using Redi-earth growing medium having a pH of 6.1. One tomato seed was planted in each cell of the trays. Each tray contained eight observations/replications, which included a non-treated control and 3 treatments. Treatment 1 contained atrazine-loaded MCC particles applied at rate equivalent to 1 kg/ha. Treatments 2 and 3 contained two and four times that rate of atrazine, respectively. Atrazine-loaded MCC particles were evenly distributed around each seed in the growing medium at the depth of planting. Each tray was watered twice per day on average, using deionized water and Peters Excel@ 15-5-15 fertilizer as needed. The greenhouse was maintained at 25° C. during the day and 20° C. at night on a 14-hour photoperiod.

Figure 3:
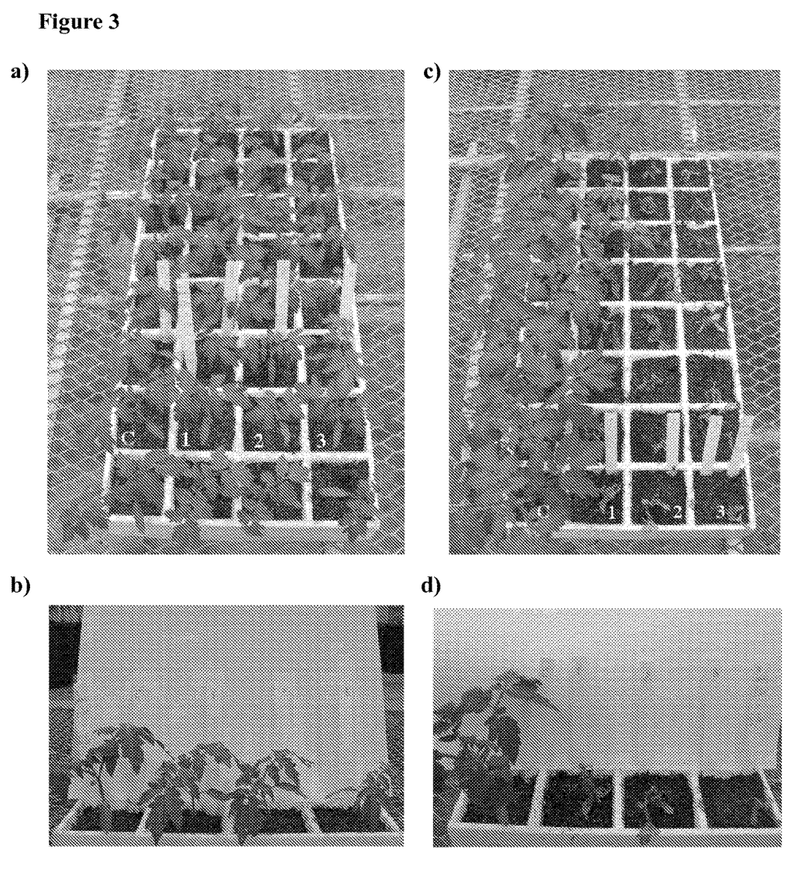
FIG. 3 shows tomato plants treated with microcapsules produced from MCC treated with the herbicide atrazine and coated with Eudragit® FS 30D: a) and b) 21 days after planting and prior to pH trigger; c) and d) 31 days after planting and 10 days after pH trigger.

Seedling emergence was observed at 10 days after planting. The pH was then raised to trigger the release of atrazine by watering two times with approximately 1 L of 0.1 M PBS (pH 7.8) applied in two aliquots each time. The regular watering regime was then resumed. Pictures were taken to document the results of the triggered release at 21 days after planting. FIGS. 3(a) and 3(b) are tomato plants prior to the triggered release. FIGS. 3(c) and 3(d) show plants 10 days after the triggered release of the AI. Some reduction in plant growth was observed prior to the application of PBS that was attributed to uneven coating of the microspheres. Ten days after the application of the PBS trigger, all tomato plants were killed except for the non-treated control, illustrating controlled release of an AI herbicide using a pH trigger solution.

Example 4

Triggered Release of Thiamethoxam

To conduct a study on the triggered release of AI under greenhouse and growth chamber conditions, 1 mm MCC particles were loaded with the insecticide thiamethoxam as follows.

Thiamethoxam-loaded MCC particles were prepared by spraying a solution (0.3 g of thiamethoxam, 80 mL of ethanol, 20 mL of water) onto 1 mm MCC (100 g) in a conventional coating pan. The Thiamethoxam-loaded MCC were coated with Eudragit® FS 30D the same way as described for Rhodamine in Example 1.

8 replications of Tomato 'Facundo' seeds were sown in three 50-cell seedling trays. The trays were filled with Redi-earth™ growing medium with a pH of 6.1. Plants were spatially arranged to avoid crowding. The trays were organized as follows: Nontreated-control (plants not treated with AI); Treatment 1 (plants treated with thiamethoxam loaded-MCC coated with Eudragit® FS 30D microspheres, phosphate buffer solution was not added to trigger release of the AI); and Treatment 2 (plants treated with -thiamethoxam loaded-MCC coated with Eudragit® FS 30D microspheres, phosphate buffer was added to trigger release of the AI).

Thiamethoxam-loaded MCC coated with Eudragit® FS 30D microspheres were evenly distributed around each seed in the growing medium. Each tray was then watered with deionized water approximately twice a day, and with Peters Professional™ 15-16-17 fertilizer as needed. The greenhouse was maintained at 25-30° C. (day) and 20-25° C. (night) with a 14-hour photoperiod.

Seedling emergence was observed 8 days after planting. 28 days after planting, the release of thiamethoxam was triggered by watering the trays two times with approximately 1 L of 0.1 M phosphate buffer solution (PBS) with a of pH 7.8. The PBS was applied in several aliquots. A regular watering regime was then resumed. Seven days after triggering the thiamethoxam release, the plants were infested with Greenhouse Whiteflies (GHWF). Whitefly adults were released into an enclosed growth chamber onto the plants to lay eggs. Neither the number of adults released nor the number of eggs laid was quantified. One week later, a single leaflet from each plant was evaluated for living and dead GHWF instars. The results of the living and dead GHWF count are shown in Table 1. The number of living whiteflies per living plant was less in both treatment 1 and 2, while treatment 2 (triggered) had the greatest percent mortality. Thus the triggered release of the AI thiamethoxam had the best performance of all treatments.

TABLE 1

Release of thiamethoxam triggered by pH shift.

| Treatment | Trigger | Number of insects per plant | | Mortality, % |
|---|---|---|---|---|
| | | Alive | Dead | |
| Nontreated Control | no | 59 ± 6.7 | 2 ± 0.6 | 3 ± 0.8 |
| Treatment 1 | no | 9 ± 1.6 | 4 ± 1.0 | 32 ± 6.0 |
| Treatment 2 | yes | 2 ± 0.7 | 3 ± 0.8 | 61 ± 7.2 |

All publications and patent applications mentioned in this specification are herein incorporated by reference to the same extent as if each independent publication or patent application was specifically and individually indicated to be incorporated by reference.

What is claimed is:

1. A method of improving the growth of a plant, said method comprising applying to a seed or locus thereof a composition comprising an active ingredient and a pH-dependent film-forming polymer, followed by exposing said composition to an appropriate pH to release said active ingredient, wherein said exposing comprises applying a release composition to said seed or locus thereof to release the active ingredient from the said composition comprising the active ingredient and the pH-dependent film-forming polymer.

2. The method of claim 1, wherein said composition is a microcapsule.

3. The method of claim 1, wherein said active ingredient is an agrochemical, an attractant, a repellent, or a bait.

4. The method of claim 3, wherein said agrochemical is a pesticide, insecticide, nematicide, acaricide, miticide, bactericide, fungicide, herbicide, plant growth regulator, fertilizer or agrochemical with phytotoxic properties.

5. The method of claim 4, wherein said pesticide is abamectin or thiamethoxam.

6. The method of claim 4, wherein said fungicide is mefenoxam, fludioxonil, a strobularin, thiabendazole, or a triazole.

7. The method of claim 4, wherein said herbicide is atrazine.

8. The method of claim 4, wherein said plant growth regulator is a triazole selected from the group consisting of uniconazole, paclobutazol, cyproconazole, propiconazole, and trinexapac-ethyl.

9. The method of claim 1, wherein said pH-dependent film-forming polymer is a polyacrylamide, a cellulose ester phthalate, cellulose ether phthalate, polyvinyl acetate phthalate, cellulose acetate trimellitate, hydroxypropyl methylcellulose acetate succinate, shellac, ammoniated shellac; a cross-linked amino resin based on urea-formaldehyde, melamine-formaldehyde, benzoguan-formaldehyde, glycoluril-formaldehyde, or an etherified polymer with incorporated free carboxylic groups or base-cleavable ester or thioester moiety; acrylic and methacrylic acids and their esters copolymers'or methyl acrylate-methacrylic acid copolymer, methyl methacrylate-methacrylic acid copolymer, or methacrylic acid-methyl acrylate-methyl methacrylate copolymer.

10. The method of claim 1, wherein said plant is a vegetable plant, an ornamental plant, a cereal; a beet; a leguminous plant; or an oil plant.

11. The method according to claim 1, wherein the improving the growth comprises improving the vigor of the plant.

12. The method according to claim 1, wherein the improving the growth comprises combating or controlling pests of the plant.

13. The method according to claim 1, wherein the composition is applied to the seed.

14. The method according to claim 1, wherein the locus is soil.

15. The method according to claim 1, wherein the composition comprises two or more active ingredients.

16. The method of claim 1, wherein said composition further comprises an inert particulate carrier.

17. The method of claim 16, wherein said inert particulate carrier is microcrystalline cellulose or porous or non-porous particulates.

18. The method of claim 17, wherein said agrochemical is dispersed in or applied to said inert particulate carrier.

19. The method of claim 3, wherein said agrochemical is encapsulated by said pH-dependent film-forming polymer.

* * * * *

UNITED STATES PATENT AND TRADEMARK OFFICE
CERTIFICATE OF CORRECTION

PATENT NO. : 9,986,738 B2
APPLICATION NO. : 13/642343
DATED : June 5, 2018
INVENTOR(S) : Alan Taylor et al.

It is certified that error appears in the above-identified patent and that said Letters Patent is hereby corrected as shown below:

Column 13, Line 15, replace "copolymers' or methyl" with --copolymers, or methyl--.

Signed and Sealed this
Twenty-fourth Day of July, 2018

Andrei Iancu
*Director of the United States Patent and Trademark Office*